United States Patent [19]

Marcus

[11] Patent Number: 5,101,978

[45] Date of Patent: Apr. 7, 1992

[54] FLUIDIC SORTING DEVICE FOR TWO OR MORE MATERIALS SUSPENDED IN A FLUID

[75] Inventor: Ira A. Marcus, Rockville, Md.

[73] Assignee: The United States of America as represented by the Secretary of the Army, Washington, D.C.

[21] Appl. No.: 441,781

[22] Filed: Nov. 27, 1989

[51] Int. Cl.$^5$ .............................................. B07C 5/02
[52] U.S. Cl. ................................... 209/3.1; 209/552; 209/576; 209/906; 209/939; 356/39
[58] Field of Search ................ 209/3.1, 539, 543, 551, 209/576, 906, 579, 3.2, 552, 939; 356/39, 23

[56] References Cited

U.S. PATENT DOCUMENTS

| | | | |
|---|---|---|---|
| 3,560,754 | 2/1971 | Kamentsky | 209/906 X |
| 3,984,307 | 10/1976 | Kamentsky et al. | 209/906 X |
| 4,009,782 | 3/1977 | Grimshaw | 209/906 X |
| 4,175,662 | 11/1979 | Zold | 209/906 X |
| 4,338,024 | 7/1982 | Bolz et al. | 356/39 |
| 4,361,400 | 11/1982 | Gray et al. | 356/23 |
| 4,756,427 | 7/1988 | Göhde et al. | 209/3.1 |
| 4,778,593 | 10/1988 | Yamashita et al. | 209/3.1 |
| 4,786,165 | 11/1988 | Yamamoto et al. | 356/23 |
| 4,887,721 | 12/1989 | Martin et al. | 209/3.1 X |

Primary Examiner—Donald T. Hajec
Attorney, Agent, or Firm—Saul Elbaum; Freda L. Krosnick

[57] ABSTRACT

A fluidic sorting device for the separation of two or more visually different materials or materials which react differently to an externally applied force. These materials are suspended in a fluid. The device comprises a fluidic logic element to which a machine vision apparatus is connected. The machine vision apparatus may be programmed to identify specific particulate materials. The machine vision apparatus captures an image of a particle or material, interprets the image, then makes subsequent value judgements, and decides as to whether the particle is to be separated out. The decision of the machine vision apparatus controls a fluidic logic element which facilitates the separation of the particles or materials. The machine vision apparatus may, optionally, comprise a counter. The novelty of the invention lies with the combination of fluidics with a machine vision apparatus.

7 Claims, 1 Drawing Sheet

FLUIDIC SORTING DEVICE FOR TWO OR MORE MATERIALS SUSPENDED IN A FLUID

RIGHTS OF THE GOVERNMENT

The invention described herein may be manufactured, used and licensed by or for the U.S. Government for governmental purposes without the payment to me of any royalties thereon.

BACKGROUND OF THE INVENTION

The present invention relates to a fluidic sorting device for the separation of two or more different materials or particles which are suspended in a fluid. The materials or particles to be separated may differ based on shape, texture, color, or any other visually distinctive characteristics. The particles may additionally differ in their visual reaction to an externally applied force, for example an electrostatic or magnetic field. The sorting device of the present invention comprises a fluidic logic element and a machine vision apparatus. An example of such a device is one which may sort different cells in the blood.

This invention enables one to program the apparatus to identify certain characteristics of particles. The function of the sorting device herein is to enable programmable automated sorting of a mixture of different particles or biological elements suspended in a fluid medium.

The use of fluidic assemblies for the sorting of various materials, for example chromosomes, is well known. U.S. Pat. No. 4,361,400, issued to Gray et al., teaches such an assembly. As a matter of fact, the Gray et al. reference further teaches, at column 6, lines 1–4, that their fluidic assembly sorting apparatus may use an optical sensor/detector.

The invention herein may be distinguished over the Gray et al. reference in that the Gray et al. patent is directed toward the sorting of chromosomes and may only be extended to sort particles of similar size. The reference apparatus further requires that the particle stream be broken up into droplets. Hence, the use of the sorting device patented by Gray et al. is limited to particles which can be encapsulated into a droplet. The invention herein is not so limited.

In addition, U.S. Pat. No. 4,361,400 requires the presence of a vibrating nozzle or a mechanism of some sort in which to form the required droplets. The invention herein uses no nozzle to break up any fluid flow. As a matter of fact, the present invention utilizes a continuous flow of suspended materials or particles in a liquid means and has no droplet formation requirement.

The patented invention further tags the solid particles in order to better identify them to be separated. This is done by electronic charge or by the use of fluorescent stain. The present invention has no such requirement. The invention herein separates the particles based on their natural appearance or on their natural reaction to being subjected to an external force such as a magnetic or electrostatic field.

Although reference has been made to blood cells or chromosomes, these particles have been used merely by way of example, and not with any intent to limit the invention to sorting only them. The present invention may be used to sort many different types and sizes of materials or particles. This invention is not limited to the separation or sorting of small particulate matter.

BRIEF SUMMARY OF INVENTION

This invention consists of a fluidic sorting device for the separation of two or more materials suspended in a fluid. The sorting device comprises a fluidic logic element and a machine vision apparatus.

The present invention makes use of two conventional components which are combined to create the apparatus of this application. The components are a fluidic sorting device and a machine vision apparatus. No novelty lies in either one of the components per se. The combination and use of these two components is the subject of this patent.

The fluidic logic element comprises one input port, two control ports and two output ports. This fluidic logic element is, as stated above, conventional and may be produced using conventional micromachining technology or any other conventional means. The physical size of the fluidic logic element is selected so as to accomodate the sizes of the particles to be sorted. Said fluidic logic element may be composed of semi-conductor materials, such as silicon and gallium arsenide. The fluidic device need not be limited to a semi-conductor material. It may alternatively be composed of metallic laminates. In order for the machine vision apparatus to capture an image of the particles flowing therethrough, the top surface cover over the fluidic logic device is composed of a transparent material. The material of which this transparent layer is composed is not critical to the present invention.

As mentioned, the particles to be separated may be visually distinct based on size, color, texture or shape. Further, the particles may be visually distinguished from one another based on their reactions/interactions to external forces. Various particulate materials react/interact differently to said forces; hence, they may additionally be separated based on their reactions/interactions (i.e. attraction, repulsion, spinning, etc.) to the outside force. Separation based on the reaction of various particulate matter to external forces requires that said external forces (i.e. magnetic or electrostatic fields) be applied to the neck area of the fluidic logic element before or within the viewing area of the machine vision apparatus and before the fluidic logic element control ports. The external forces to be applied are well within the skill of the artisan; their sources are conventional.

The machine vision apparatus of the type used herein is programmable. This equipment, cameras, computers, displays, and software, is conventional and commercially available. It may be programmed to identify and interpret different images suspended in a fluid medium. The conventional machine vision apparatus used herein consists of a camera, an image capture function, an image interpretation function, a decision control function, and an optional counter. It is capable of identifying the various particles to be separated and to convey this message to control ports in the fluidic logic element. Said machine vision instructs a fluidic controller on how the particulate matter should be sorted. The machine vision apparatus may be equipped with a magnification lens or a microscope in order to better accommodate a wide range of particle sizes to be separated; and hence, be able to perform in a variety of different separation tasks.

It is an object of the present invention to produce a fluidic sorting device which uses a machine vision apparatus to identify the particles or materials to be separated.

It is an object of the present invention to produce a sorting device which is programmable.

It is a further object of the invention to produce a sorting device whose basic hardware apparatus may be used for the sorting of a variety of different particles in different fluid bases.

It is a further object of the invention to create an efficient particulate or material sorting apparatus from the use of conventional and commercially available components.

Yet another object of the invention is to produce an apparatus which can be used for sorting and separating applications of a wide magnitude.

Other objectives and features of the present invention will be apparent from the following detailed description of the invention, drawings and claims.

Figure 1:
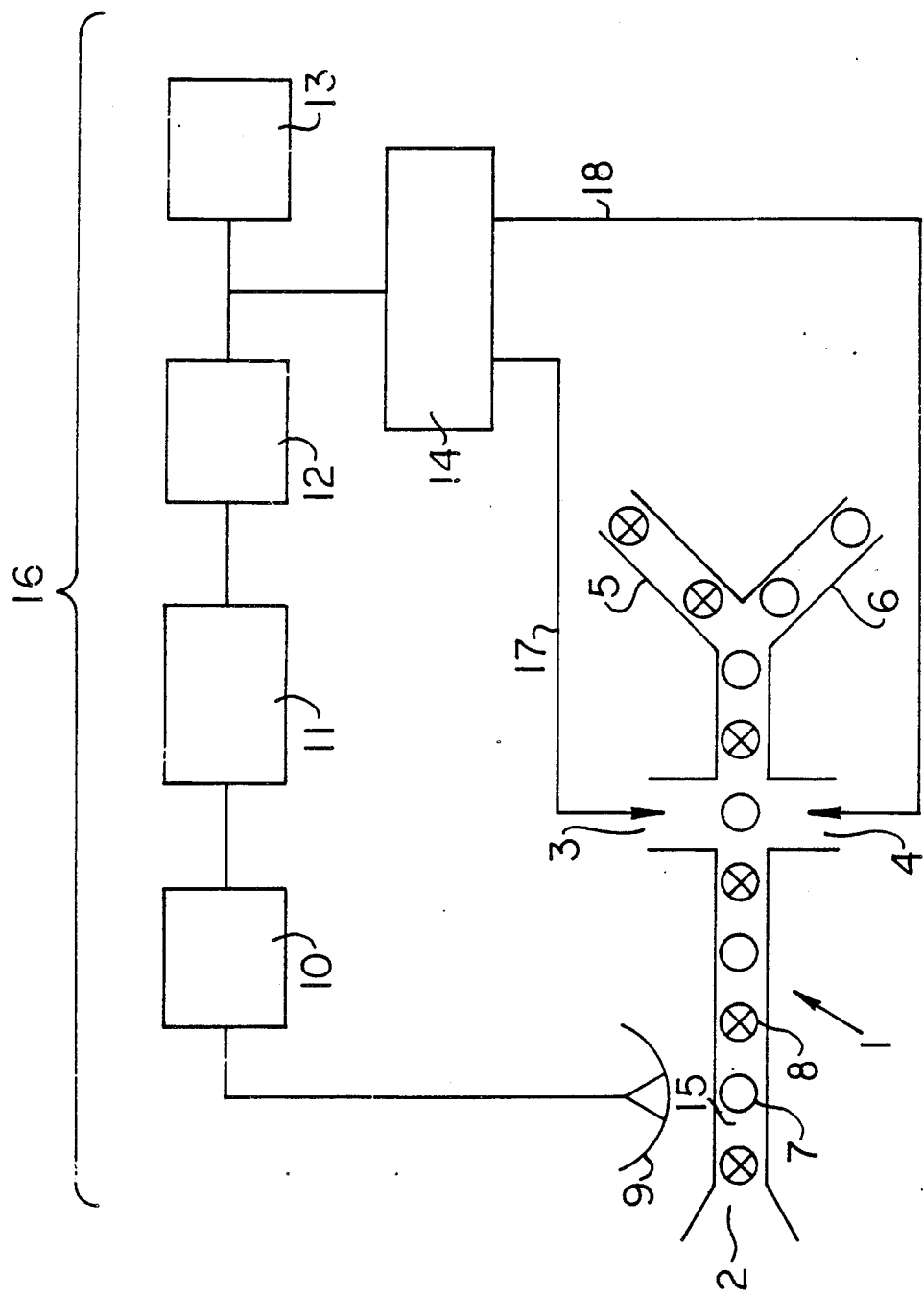
FIG. 1 is a schematic diagram of a fluidic sorting device of the present invention.

Reference will now be made to the embodiments of the invention.

DETAILED DESCRIPTION OF THE INVENTION

FIG. 1 generally teaches the apparatus and concept of the present invention. In said figure, element 1 broadly depicts the fluidic logic element. Said fluidic logic element 1 comprises input flow port 2 through which a suspension containing particulate matter is forced. Fluidic logic element 1 further comprises control port A and control port B, 4 and 3, respectively; and output port A and output port B, 5 and 6, respectively. To said fluidic logic element 1, is connected a machine vision apparatus which is set forth broadly at 16. The machine vision apparatus 16 consists of a machine vision camera lens 9, an image capture device 10, an image interpretation device 11, and a decision control device 12. Said machine vision apparatus may further comprise an optional, conventional counter device 13. Connected to the decision control device 12 is a fluidic controller device 14 which transmits using leads 17 and 18 the input signal from the control decision device 12 to the fluidic element control ports 3 and 4. The input signal instructs the control ports 3 and 4 as to how the particulate materials 7 and 8 should be sorted.

A suspension containing at least two visually different particulate matter is forced through input flow port 2. The suspension contains particle type A, 8, particle type B, 7, and a fluid carrier 15. Machine vision camera lens 9 reads the appearance of said particles 7 and 8. It transmits what is read to an image capture device 10 which forwards what it sees to an image interpretation device 11 which is able to interpret and register a distinction between particles 7 and 8. This distinction is then transmitted to a control decision device 12 which signals a fluidic controller device 14 to instruct control ports A and B, 4 and 3 respectively, to separate out said particles 7 and 8. These particles 7 and 8 are then sorted through output port A and output port B, 5 and 6.

The present invention may be used to separate many different types of particulate and non-particulate materials. The apparatus of the present invention may be used to separate any material so long as there exists visual distinctions between the materials to be separated. The apparatus can be adjusted or altered to accommodate various types of materials. For example, the size of the fluidic logic element used would depend upon the materials one wishes to sort.

The dilution of the suspended materials or particles, and the timing and flow rate control of the suspensions should be such as to allow the suspended materials to be properly diverted to the desired port.

The apparatus herein may be used, for example, to sort different components of the human blood. The components of the human blood differ in both shape and size. Note that the sizes of the major components of the human blood are as follows:

| | |
|---|---|
| Red corpuscles (erythrocytes) | $7.5 \times 10^{-3}$ mm |
| White corpuscles (leukocytes) | $8.3 \times 10^{-3}$ mm |
| Platelets (thrombocytes) | $2.5 \times 10^{-3}$ mm |

These blood particles do differ in shape, and differ somewhat in size. The apparatus of the present invention would detect the variations between the particles and would sort the particles accordingly. The separation of said particles would be of great value in the medical field of research. The present invention would also find use in the separation of sickle blood cells from the blood. The blood may be purified or relieved of any contaminants through the use of the apparatus herein.

Blood particles may be separated out based on their shape, color or other features. For example, red blood cells are round disks which are concave on two sides; whereas, blood platelets are smaller in size, are round and are non nucleated bodies. This type of separation can be accomplished using the present invention. The machine vision apparatus need only be programmed in order to pick up on said distinguishing features—i.e., size, color, shape.

The particles to be sorted may also be distinguished from one another by means other than their physical appearance. They may be distinguishable based on their reaction to external forces, such as magnetic or electrostatic fields. Their reaction/interaction with said forces could be visually detected and interpreted by the machine vision apparatus which would direct the particles to their appropriate output port. Separation based on the reaction/interaction of various particulate matter to externally applied forces requires that said external forces be applied to the neck area of the fluidic logic element.

The machine vision camera lens may be fitted to allow magnification of a particle from about 100 to 1000 times. This allows the machine vision camera to better transmit the properties of the particles or materials it sees.

The fluidic sorting apparatus herein may be used to separate more than two visually distinct particles. Each output port may be modified so that it is used as a fluidic logic element. To said second fluidic logic element a machine vision apparatus is set up in the same manner set forth in FIG. 1. The sorting or separation may be done serially in a cascading manner. The suspensions exiting from the output ports would be further analyzed by the machine vision apparatus and sorted accordingly. This would find use in the purification of materials.

The specific particles disclosed above are merely set forth as representative examples which fall within the scope of use of the present invention.

Although the invention has been described with reference to specific embodiments and drawing, it is to be understood that the invention herein is not limited to those precise embodiments. Various changes and modifications may be effected by one skilled in the art without departing from the scope or spirit of the present invention.

I claim:

1. A sorting device for the separation of two or more visually distinguishable materials which are suspended in a fluid, said sorting device comprising:

a fluidic logic element consisting essentially of a supply stream input port connected to a fluid suspension supply means, a first control port, a second control port, a first output port and a second output port; and a machine vision apparatus comprising an image capture device, an image interpretation device and a fluidic controller device;

said machine vision apparatus is connected to said fluidic logic element at said first and said second control ports and sends signals to and operates said control ports.

2. The sorting device in accordance with claim 1, wherein said machine vision apparatus further comprises a counter means.

3. The sorting device in accordance with claim 1, wherein said fluid suspension supply means contains a fluid having at least two visually distinguishable materials suspended therein.

4. The sorting device in accordance with claim 1, wherein the visually distinguishable suspended materials to be separated are visually distinguishable based on the color of said suspended materials.

5. The sorting device in accordance with claim 1, wherein the visually distinguishable suspended materials to be separated are visually distinguishable based on the size of said suspended materials.

6. The sorting device in accordance with claim 1, wherein the visually distinguishable suspended materials to be separated are visually distinguishable based on the shape of said suspended materials.

7. The sorting device in accordance with claim 1, wherein the visually distinguishable suspended materials to be separated are visually distinguishable based on their visible reaction to an externally applied force.

* * * * *